(12) United States Patent
Schaudies et al.

(10) Patent No.: US 7,070,935 B2
(45) Date of Patent: Jul. 4, 2006

(54) METHOD FOR DETECTING A BIOLOGICAL ENTITY IN A SAMPLE

(75) Inventors: Robert Paul Schaudies, Rockville, MD (US); Doreen Robinson, Laurel, MD (US)

(73) Assignee: Science Applications International Corporation, San Diego, CA (US)

( * ) Notice: Subject to any disclaimer, the term of this patent is extended or adjusted under 35 U.S.C. 154(b) by 166 days.

(21) Appl. No.: 10/630,384

(22) Filed: Jul. 30, 2003

(65) Prior Publication Data

US 2004/0096879 A1    May 20, 2004

Related U.S. Application Data

(63) Continuation of application No. 09/563,038, filed on May 1, 2000, now abandoned.

(60) Provisional application No. 60/190,691, filed on Mar. 20, 2000, provisional application No. 60/183,388, filed on Feb. 18, 2000.

(51) Int. Cl.
*C12Q 1/68* (2006.01)
*C12P 19/34* (2006.01)
*C07H 21/02* (2006.01)

(52) U.S. Cl. .................. 435/6; 536/23.1; 435/91.1; 435/91.2

(58) Field of Classification Search ............... 435/6; 536/23.1, 24.3
See application file for complete search history.

(56) References Cited

U.S. PATENT DOCUMENTS

| | | | |
|---|---|---|---|
| 5,043,272 A | 8/1991 | Hartley | 435/91 |
| 5,106,727 A | 4/1992 | Hartley et al. | |
| 5,632,957 A | 5/1997 | Heller et al. | |
| 5,773,210 A | 6/1998 | Crowl et al. | |
| 5,800,992 A | 9/1998 | Fodor et al. | |
| 5,821,060 A | 10/1998 | Arlinghaus et al. | |
| 5,837,832 A | 11/1998 | Chee et al. | |
| 5,858,659 A | 1/1999 | Sapolsky et al. | |
| 5,858,661 A | 1/1999 | Shiloh | |
| 5,861,242 A | 1/1999 | Chee et al. | |
| 5,871,928 A | 2/1999 | Fodor et al. | |
| 5,925,522 A | 7/1999 | Wong et al. | |
| 5,925,525 A | 7/1999 | Fodor et al. | |
| 5,929,208 A | 7/1999 | Heller et al. | |
| 5,994,058 A | 11/1999 | Senapathy | |
| 6,013,440 A | 1/2000 | Lipshutz et al. | |
| 6,027,880 A * | 2/2000 | Cronin et al. | 435/6 |
| 6,156,502 A | 12/2000 | Beattie | |

FOREIGN PATENT DOCUMENTS

| | | |
|---|---|---|
| EP | 0 950 720 A1 | 10/1999 |
| WO | WO 96/41893 | 12/1996 |
| WO | WO 97/22720 | 6/1997 |
| WO | WO99/22023 | 5/1999 |
| WO | WO 02/061659 | 8/2002 |

OTHER PUBLICATIONS

Peng et al, "Multiple PCR analyses on trace amounts of DNA extracted from fresh and paraffin wax embedded tissues after random hexamer primer PCR amplification", J. Clin. Pathol. (1994) 47:605-608.*

See http://www.psrast.org/soilfertfact.htm (accessed Jun. 7, 2005).*

Written Opinion for Application No. PCT/US01/04104, dated May 30, 2003 (mailing date).

Iyer, L., et al., "Adaptations of the Helix-Grip Fold for Ligand Binding and Catalysis in the START Domain Superfamily," *Proteins: Structure, Function, and Genetics*, vol. 43, pp. 134-144 (2001).

Kitazoe, Y., et al., "A New Theory of Phylogeny Inference Through Construction of Multidimensional Vector Space," *Mol. Biol. Evol.*, vol. 18, No. 5, pp. 812-828 (2001).

Geourjon, C., et al., "Identification of Related Proteins With Weak Sequence Identity Using Secondary Structure Information," *Protein Science*, vol. 10, pp. 788-797 (2001).

Anantharaman, V., et al., "Regulatory Potential, Phyletic Distribution and Evolution of Ancient, Intracellular Small-Molecule-Binding Domains," *J. Mol. Biol.*, vol. 307, pp. 1271-1292 (2001).

Liberles, D., et al., "The Adaptive Evolution Database (TAED)," *Genome Biology*, vol. 2, No. 4, pp. preprint/0003.1-0003.18, 2001.

Tatusov, R., et al., "The COG Database: New Developments in Phylogenetic Classification of Proteins From Complete Genomes," *Nucleic Acids Research*, vol. 29, No. 1, pp. 22-28 (2001).

Anantharaman, V., et al., "TRAM, a Predicted RNA-Binding Domain, Common to tRNA Uracil Methylation and Adenine Thiolation Enzymes," *FEMS Microbiology Letters*, vol. 197, pp. 215-221 (2001)

(Continued)

*Primary Examiner*—Jeffrey Fredman
(74) *Attorney, Agent, or Firm*—Kilpatrick Stockton LLP

(57) ABSTRACT

The invention relates to the detection of a biological entity in a sample. More particularly, the invention relates to detection of specific pathogens from a possible presence of hundreds to thousands of distinct biological species. The invention provides new assays that can detect the presence of one or more biological entity in a sample out of a possible number of hundreds to thousands of distinct biological species. The method according to the invention for detecting a biological entity in a sample comprises randomly amplifying nucleic acids in the sample to produce labeled nucleic acids; hybridizing the labeled nucleic acids to an array of predetermined nucleic acids; and detecting the labeled nucleic acids that have hybridized to the array.

104 Claims, 1 Drawing Sheet

OTHER PUBLICATIONS

Liu, Q., et al., "DNA Computing on Surfaces," *Nature*, vol. 403, pp. 175-179, Jan. 13, 2000.

Woese, Carl R., "Interpreting the Universal Phylogenetic Tree," *Proc. Natl. Acad. Sci.*, vol. 97, No. 15, pp. 8392-8396, Jul. 18, 2000.

Aravind, L., et al., "The a/β Fold Uracil DNA Glycosylases: A Common Origin With Diverse Fates," *Genome Biology*, vol. 1, No. 4, pp. research0007.1-0007.8 (2000).

Natale, D., et al., "Towards Understanding the First Genome Sequence of a Crenarchaeon by Genome Annotation Using Clusters of Orthologous Groups of Proteins (COGs)," *Genome Biology*, vol. 1, No. 5, pp. research0009.1-0009.19 (2000).

Grech, A., et al., "Complete Structural Characterisation of the Mammalian and *Drosophila* TRAF Genes: Implications for TRAF Evolution and the Role of RING Finger Splice Variants," *Molecular Immunology*, vol. 37, pp. 721-734 (2000).

Adleman, Leonard, M., "Computing With DNA," *Scientific American*, vol. 279, pp. 54-61, Aug., 1998.

Hacia, J. G., et al., "Strategies for Mutational Analysis of the Large Multiexon ATM Gene Using High-Density Oligonucleotide Arrays," *Genome Research*, vol. 8, pp. 1245-1258 (1998).

Ramsay, G., "DNA Chips: State-of-the-Art," *Nature Biotechnology*, vol. 16, pp. 40-44 (1998).

Adleman, Leonard, M., "Molecular Computation of Solutions to Combinatorial Problems," *Science*, vol. 266, pp. 1021-1024, Nov. 11, 1994.

Atschul, Stephen, et al., "Basic Local Alignment Search Tool," *J. Mol. Biol.*, vol. 215, pp. 403-410 (1990).

International Search Report for Application No. PCT/US01/04104 dated May 6, 2002 (mailing date).

Guschin, Dmitry Y., et al., "Oligonucleotide Microchips as Genosensors for Determinative and Environmental Studies in Microbiology", *Applied and Environmental Microbiology*, vol. 63, No. 6, pp. 2397-2402, Jun. 1997.

Kahl Gunter, Dictionary of Gene Technology, VCH Publishers, Inc., New York, NY (USA), Jun. 1995.

Boehringer Mannheim, 1998 Biochemical Catalog, GmbH printed in Germany, Jan. 1998.

Bej et al., Multiplex PCR amplification and immobilized capture probes for detection of bacterial pathogens and indicators in water; *Molecular and Cellular Probes*, vol. 4, pp. 353-365; Dec. 1990.

Hacia, J.G. et al. (1998) "Evolutionary Sequence Comparisons Using High-Density Oligonucleotide Arrays"; *Nature Genetics;* 18:155-158.

Hacia, J.G. et al. (1998) "Strategies for Mutational Analysis of the Large Multiexon ATM Gene Using High Density Oligonucleotide Arrays"; *Genome Research*, 8:1245-1258.

Head, S.R. et al. (1999); "Solid-Phase Sequence Scanning for Drug Resistance Detection in Tuberculosis"; *Molecular and Cellular Probes*; 13:81-87.

Tetenius et al., "Degenerate oligonucleotide primed PCR: General amplification of target DNA by a single degenerate primer", *Genomics* (1992) 13:718-725.

Sayada et al., "Genomic fingerprinting of Yersinia enterocolitica species by degenerate oligonucleotide primed polymerase chain reaction", *Electrophoresis* (1994) 15:562-565.

Muller et al., "Defining ancestral karyotype of all primates by multidirectional chromosome painting between tree shrews, lemurs and humans", *Chromosoma* (1999) 108:393-400.

Castellino, A.m. (1997) "When the Chips are Down", *Genome Research* 7:943-946.

Grattard, F et al. (1994) "Arbitrarily Primed PCR, Ribotyping, and Plasmid Pattern Analysis Applied to Investigation of a Nosocomial Outbreak Due to *Enterobacter cloacoe* in a Neonatal Intensive Care Unit"; *Journal of Clinical Microbioloty* 32(3):596-602.

Hacia, J.G. et al. (1996) "Detection of Heterozygous Mutations of BRCA1 Using High Density Oligonucleotide Arrays and Two-Colour Fluorescence Analysis"; *Nature Genetics* 14:441-447.

Ramsay, G. (1998) "DNA Chips: State-of-the-Art"; *Nature Biotechnology* 16:40-44.

Schena, S. (1996) "Genome Analysis with Gene Expression Microarrays"; *BioEssays* 18(5):427-431.

Struelens, M.D., M.J. et al. (1998) Comparative and Library Epidemiological Typing Systems: Outbreak Investigations Versus Surveillance Systems:, From the Fifth International Conference on the Prevention of Infection; *Infection Control and Hospital Epidemiology* 19(8):565-569.

Tang, K. et al. (1999) "Chip-Based Genotyping by Mass Spectrometry (DNA Chip/Single Nucleotide Polymorphism)"; *Proc. Natl. Acad. Sci USA* 96L19916-10020.

Wallraff, G. et al. (1997) "DNA Sequencing on a Chip (This Method, Which Combined Semiconductor Manufacturing Technology with Molecular Biology, Has Been Used to Build DNA and RNA Arrays at Densities as High as $10^6$ sites/cm$^2$)", *Chemtech*; Feb. 1997:22-32.

Welsh, J. et al. (1990) "Fingerprinting Genomes Using PCR with Arbritary Primers"; *Nucleic Acids Research* 18(24):7213-7218.

Noonan, K.E. et al., *Nucl. Acids. Res.* 16:10366 (1988).

Feinberg, A.P. et al., *Anal. Biochem.* 132:6-13 (1983).

Liang, W. et al., *Nucl. Acids Res.* 16:3579 (1988).

Mullis, K.E. et al., *Cold Spring Harb. Symp. Quant. Biol.* 51:263-73 (1986).

Loh et al., *Science* 243:217-200 (1988).

Landegren, U et al., *Sciencel* 242:229-237 (1988).

Mullis, K.B. et al. *Meth. Enzymol.* 155:335-350 (1987).

Maniatis et al., *Molecular Cloning: A La. Manual*, Cold Spring Harbor Lab., NY (1982), pp. 129 & 131.

Caetano-Anolles, G., Amplifying DNA with Arbitrary Oligonucleotide Primers, *PCR Methods and Applications*, 1993, pp. 85-104, Cold Spring Harbor Laboratory Press.

Caetano-Anolles, G., "Enhanced detection of polymorphic DNA by multiple arbitrary amplicon profiling of endonuclease-digested DNA: identification of markers tightly linked to the supermodulation locus in soybean", *Mol. Gen. Genet.*, 1993, pp. 57-64, vol. 241.

Caetano-Anolles, G., "DNA Amplification Fingerprinting Using Arbitrary Oligonucleotide Primers", *Applied Biochemistry and Biotechnology*, 1993, pp. 189-194, vol. 42.

Caetano-Anolles, G., "Primer-template interactions during DNA amplification fingerprinting with single arbitrary oligonucleotides", *Mol. Gen. Genet.*, 1992, pp. 157-165, vol. 235.

* cited by examiner

METHOD FOR DETECTING A BIOLOGICAL ENTITY IN A SAMPLE

This application is a continuation of Ser. No 09/563,038 filed May 1, 2000 now abandoned, which claims benefit of Provisional application Ser. No. 60/190,691 filed Mar. 20, 2000 and claims benefit of Provisional application Ser. No. 60/183,388 filed Feb. 18, 2000.

BACKGROUND OF THE INVENTION

1. Field of the Invention

The invention relates to the detection of a biological entity in a sample. More particularly, the invention relates to detection of specific pathogens from a possible presence of one to hundreds to thousands of pathogens.

2. Summary of the Related Art

Crowding and unrest in the modern world has created the potential for rapid spread of disease, either through terrorism in the form of germ warfare, or simply through disease transmission among densely packed hosts in urban environments. Wade, New York Times, Nov. 21, 1997, discloses that one gram of anthrax, about the weight of two paper clips, contains enough doses to kill ten million people. Many other pathogenic organisms could similarly be used by terrorists, and it would be difficult to know which pathogens were being used before it was too late to avoid illness and death. In addition, in urban environments widespread epidemics may be more likely to happen, due to the close proximity of diseased and healthy people. In such instances, it could be critical to determine at an early stage what pathogen is involved to provide effective treatment and/or prophylaxis. Moreover, when natural disasters, such as flooding or earthquakes occur, frequently widespread disease follows in the aftermath. Effective relief requires the ability to rapidly identify any pathogen causing such an outbreak.

Unfortunately, current methodologies do not allow simultaneous screening for specific pathogens among a possible hundreds to thousands of pathogens. Current methodologies include antibody-based assays, DNA chip assays and assays based on polymerase chain reaction. Chee et al., U.S. Pat. No. 5,861,242 (1999) discloses an array of nucleic acid probes on biological chips for diagnosis of HIV. Crowl et. al., U.S. Pat. No. 5,773,210 (1998) discloses an assay for HIV utilizing an envelope protein from the virus to detect antibodies to the virus in patient's serum. Grattard et al., *J. Clin. Microbiol.* 32: 596–602 (1994) discloses the use of PCR to detect *Enterobacter cloacae* in a nosocomial outbreak. Unfortunately, all of these methodologies are limited to the detection of a single species of pathogen. There is, therefore, a need for new assays that can detect the presence of one or more biological entity in a sample out of a possible number of hundreds to thousands of distinct biological species.

BRIEF SUMMARY OF THE INVENTION

The invention provides new assays that can detect the presence of one or more biological entity in a sample which might be any one of hundreds to thousands of possible distinct biological species. The method according to the invention for detecting a biological entity in a sample comprises randomly amplifying nucleic acids in the sample to produce labeled nucleic acids; hybridizing the labeled nucleic acids to an array of predetermined nucleic acids; and detecting the labeled nucleic acids that have hybridized to the array. The method according to the invention is useful for such detection in the context of hospitals or physicians' offices, battlefield or trauma situations, emergency responders, forensic analysis, food and water monitoring, screening for indications of genetic alterations in specific organisms and environmental analysis and background characterizations.

The present invention is useful as a phylogenetic analysis. In such embodiments a continuum of highly conserved to highly specific nucleic acids are used to catagorize a multiplicity of biological entities from a single sample based upon binary pattern generated. Thus one can conclude the presence or absence of specific biological entities in the sample, as well as establish the organism's kingdom, phylum, class, order, genus species.

In preferred embodiments, the amplification step comprises a polymerase chain reaction. Preferably, the amplification step utilizes random primers four to nine nucleotides in length, most preferably four to six nucleotides in length. In certain preferred embodiments, the array of predetermined nucleic acids are immobilized on a surface. In certain preferred embodiments, the labeled nucleic acids are enzymatically detected. In certain preferred embodiments, the labeled nucleic acids are biotinylated. In certain preferred embodiments, the labeled nucleic acids are fluorescently labeled or radiolabeled. In certain preferred embodiments, the labeled nucleic acids are labeled with digoxigenin. In certain preferred embodiments, the surface on which the predetermined nucleic acids are immobilized is an opaque membrane. In certain preferred embodiments, the surface is silica-based. Preferably, the predetermined nucleic acid sequences are at predetermined positions on the array. In certain preferred embodiments the sample comprises multiple biological entities. Generally, at least one biological entity to be detected is a pathogen. In certain preferred embodiments, the predetermined nucleic acids are more than 30 nucleotides in length.

DETAILED DESCRIPTION OF THE PREFERRED EMBODIMENTS

Figure 1:
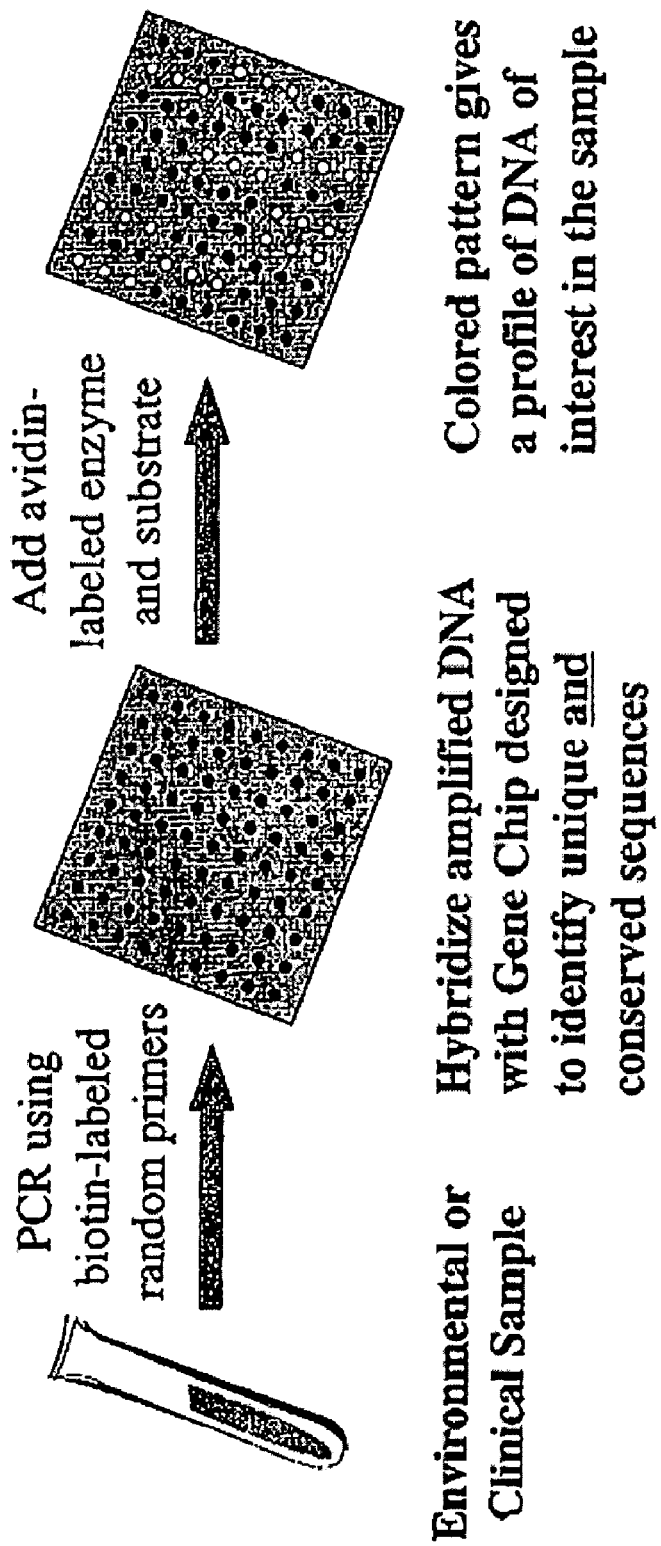
FIG. 1 shows a schematic for a preferred embodiment of the invention.

The invention relates to the detection of a biological entity in a sample. More particularly, the invention relates to detection of specific pathogens from a possible presence of hundreds to thousands of pathogens. The invention provides new assays that can detect the presence of one or more biological entity in a sample which might be any one of hundreds to thousands of possible distinct biological species.

The patents and publications recited herein reflect the level of knowledge in the field and are hereby incorporated by reference in their entirety. In the event of conflict between any such patent or publication and the present disclosure, the present disclosure shall prevail.

The method according to the invention for detecting a biological entity in a sample comprises randomly amplifying nucleic acids in the sample to produce labeled nucleic acids; hybridizing the labeled nucleic acids to an array of predetermined nucleic acids; and detecting the labeled nucleic acids that have hybridized to the array. The method according to the invention is useful for such detection in the context of hospitals or physicians' offices, battlefield or trauma situations, emergency responders, forensic analysis, food and water monitoring, screening for indications of genetic alterations in specific organisms and environmental analysis and background characterizations.

For purposes of the invention, the term "randomly amplifying" means increasing the copy number of a segment of nucleic acid in vitro using random primers, each of which are four to nine nucleotides in length, most preferably four to six nucleotides in length. "Biological entity" includes viruses, viroids, bacteria, fungi, protozoa and the like. A "sample" is any source, and can be a gas, a fluid, a solid or any mixture thereof. "Nucleic acids" means RNA and/or DNA, and may include unnatural bases. A "predetermined nucleic acid" is a nucleic acid for which the sequence is known. In certain preferred embodiments, the predetermined nucleic acids are more than 30 nucleotides in length. A "labeled nucleic acid" is a nucleic acid that can be detected. "Hybridized" means having formed a sufficient number of base pairs to form a nucleic acid that is at least partly double stranded under the conditions of detection. An "array of predetermined nucleic acids" is a multiplicity of predetermined nucleic acids (including nucleic acids complementary to a biological entity to potentially be detected) having a known spacial arrangement or relationship to each other.

In preferred embodiments, the amplification step comprises a polymerase chain reaction. Generally, conventional PCR methodology (see e.g., Molecular Biology Techniques Manual, Third Edition (1994), Coyne et al. Eds.) can be used for the amplification, except that the annealing step is preferably carried out at lower temperatures, e.g., 50–65° C. The primers utilized in the amplification step are multiple random primers of four to six nucleotides in length. Whereas longer primers are useful for the amplification of known sequences they are not suitable for the non-specific amplification of nucleic acids in a sample as long primers necessarily provide significant specificity of amplification. Use of short, random primers will allow the amplification of all nucleic acids within a given sample. Due to their short length, the primers are capable of binding to virtually all of the DNA sequences, and use of random primers (i.e. primers having different DNA sequences) further increase the likelihood that all DNA sequences will be amplified.

In certain preferred embodiments, one or more nucleoside triphosphate used in the amplification will be labeled. In certain preferred embodiments, the labeled nucleic acids are enzymatically detected. Preferred enzymes include, without limitation, alkaline phosphatase, horseradish peroxidase and any other enzyme that produces a colored product. In certain preferred embodiments, the labeled nucleic acids are biotinylated. In certain preferred embodiments, the labeled nucleic acids are fluorescently labeled or radiolabeled. In certain preferred embodiments, the labeled nucleic acids are labeled with digoxigenin. Biotinylated nucleic acid sequences are readily identified through incubation with an avidin linked colorimetric enzyme, for example, alkaline phosphatase or horse radish peroxidase. Biotin is particularly preferred in applications in which visualization is required in the absence of fluorescence-based systems. Digoxigenin labeled nucleic acid sequences are readily detected using commercially available immunological reagents. Recent advances in molecular biology, in part due to the efforts under the Human Genome Project, have spurred the development of new methods for the labeling and detection of DNA and DNA fragments. Traditionally, radioisotopes have served as sensitive labels for DNA while, more recently, fluorescent, chemiluminescent and bioactive reporter groups have also been utilized. Fluorescent and chemiluminescent labels function by the emission of light as a result of the absorption of radiation and chemical reactions, respectively. Kits and protocols for labeling the primers and/or the amplified sequences are readily available in the published literature regarding PCR amplifications. Such kits and protocols provide detailed instructions for the labeling of both primers and the amplified DNA which protocols can readily be adapted for the purposes of the method of the invention.

In certain preferred embodiments, the array of predetermined nucleic acids are immobilized on a surface. In certain preferred embodiments, the surface on which the predetermined nucleic acids are immobilized is an opaque membrane. Preferred opaque membrane materials include, without limitation, nitrocellulose and nylon. Opaque membranes are particularly preferred in rugged situations, such as battlefield or other field applications. In certain preferred embodiments, the surface is silica-based. "Silica-based" means containing silica or a silica derivative, and any commercially available silicate chip would be useful. Silica-based chips are particularly useful for hospital or laboratory settings and are preferably used in a fluorescent reader.

Preferably, the predetermined nucleic acid sequences are at predetermined positions on the array. In preferred embodiments, the predetermined nucleic acid sequences are arrayed by immobilization on a surface. Arraying the predetermined nucleic acid sequences at predetermined positions on a chip allows a chip-based approach to the detection of biological species within a given sample. The predetermined nucleic acid sequences are printed onto the chip using computer-controlled, high speed robotics, which devices are often termed "spotters". A spotter can be utilized to rapidly mass-produce identical arrays of the predetermined nucleic acid sequences on hundreds of chips. Because the location of each predetermined nucleic acid on the chip is known, hybridization, detection and localization lead to the identification of the biological entity or entities) present in the sample (see FIG. 1). In certain preferred embodiments the sample comprises multiple biological entities. Generally, at least one biological entity to be detected is a pathogen.

The invention relates to the identification of one or more biological entities in a given sample. The invention provides a method for the rapid identification of multiple biological entities simultaneously within a given sample. This contribution allows scientists, technicians and medical workers to rapidly and simultaneously identify the presence of multiple biological entities, including pathogens, in a sample taken from any source, including a human individual, a land or aquatic animal, and water, plants or foodstuffs, dirt, air, or any other environmental or forensic sample.

The method of the invention has particular application to situations of battlefield or outbreaks of disease which may be caused by a biological pathogen, as well as forensic analysis, food and water monitoring to screening for indications of genetic manipulations in specific organisms and environmental analysis and background characterizations. Using the method of the invention, any known biological pathogen could be detected in a sample, and multiple biological species can be simultaneously detected. In addition, the method is useful for the detection of biological pathogens which affect plants or animals.

The potential threat of terrorism and battlefield use of biological weapons is growing around the world. On the battlefield, multiple biological weapons may be released at one time, thus creating a situation in which field doctors should have the capability of simultaneously identify multiple biological species in a single test. Prior to applicants invention, however, no such method existed. In an urban setting, a single biological pathogen might be released over a broad area, or in a crowded location, with little or no warning as to the threat and event of this release, nor any statement as to the identity of the biological species which was released.

In either such situation referred to above, or in the event of a natural or accidental occurrence of dissemination of a biological pathogen (e.g. contamination of foodstuffs with Eschericia coli, or the spread of communicable diseases such as meningitis), the first indication of the infection of humans could be a cluster of individuals each displaying similar symptoms. However, as the initial symptoms of many biological pathogens are very similar to each other and to symptoms of the flu (e.g., headaches, fever, fatigue, aching muscles, coughing) the rapid identification of the actual biological species causing the symptoms would be a significant benefit such that prompt and proper treatment could be implemented by medical professionals. In addition, the method according to the invention can be used to assess the status of the etiologic agent with respect to drug resistance, thereby affording more effective treatment.

Examples of biological pathogens which may be used for production of biological weapons, or for use in terrorism in which event the goal of such terrorism may be to kill or debilitate individuals animals or plants, include; without-limitation, *Bacillus anthracis* (anthrax), *Yersinia pestis* (bubonic plague), *Brucella suis* (brucellosis), *Pasturella tularensis* (tularemia), *Coxiella burnetti* (Q-fever), *Pseudomonas aeriginosa* (pneumonia, meningitis), *Vibrio cholera* (cholera), *Variola virus* (small pox), *Botulinum toxin* (botulism), *Saxitoxin* (respiratory paralysis), *Ricinus communis* (ricin), *Salmonella, Staphylococcus aureus*, aflatoxin and other fungal toxins, *Shigella* (dysentery), and Yellow Fever Virus.

The present invention is useful as a phylogenetic analysis. In such embodiments a continuum of highly conserved to highly specific nucleic acids are used to catagorize a multiplicity of biological entities from a single sample based upon binary pattern generated. Thus one can conclude the presence or absence of specific biological entities in the sample, as well as establish the organism's kingdom, phylum, class, order, genus species.

In another preferred embodiment, the sample comprises multiple (more than one) biological entities. Depending upon the type of substrate chosen and the size of the chosen substrate, a chip can be arrayed with hundreds or thousands of predetermined nucleic acids in a predetermined pattern.

In another preferred embodiment, one or more of the biological entities is a pathogen. Since the method of the invention is designed to amplify all DNA within the sample, a biological species most likely will need to be present in multiple copies in order to be sufficiently amplified. If pathological entities are present in the sample in a sufficient amount to cause harm, then they will most likely be present in multiple copies and will be sufficiently amplified through the method of the invention.

To increase the confidence in the results of the biological species detected according to the method of the invention, the array will preferably include positive and negative controls and redundancies, for example multiple copies of the same nucleic acid or several distinct nucleic acids from the same target organism. The array is also useful to provide broad as well as specific identification. For example, 16s ribosomal RNA can be used to establish the presence of bacteria, conserved bacillus sequences can be used to identify bacillus presence, and specific DNA can further classify the bacillus species or strain. Any desired target biological species, including pathological species, can be included in—the array through reference to the published literature of the—DNA sequences characteristic of such organism, and then either synthesis or cloning of such published sequences.

The presence of a particular target organism within a given sample is determined by hybridizing the labeled amplified nucleic acids from the sample to the array on the chip according to well known techniques. Hybridization should preferably be conducted under high stringency conditions, as it is expected that the amplified products will be at least 30 nucleotides in length and they are being hybridized to PCR amplified gene fragments. Suitable high stringency conditions include hybridization at between 50° C. and 65° C. Then utilizing the proper means of detection to visualize the particular label used for the labeling of the amplified nucleic acids in order to identify which predetermined nucleic acid sequences were hybridized to the amplified nucleic acids. Since the chip holds an array of predetermined nucleic acids in a predetermined pattern, the pattern of hybridization will identify the biological species within the sample.

The following example(s) are intended to further illustrate certain preferred embodiments of the invention, and are not intended to be limiting in nature.

EXAMPLE 1

Preparation of a Diagnostic Array

The following steps may be used to generate arrays of predetermined nucleic acids that are fixed to a solid surface for carrying out the method of the invention. The number of predetermined nucleic acids which are included on any array can be designed according to the specific needs and desires of the user. Relative amounts of various biological entities can be ascertained by conducting sequential hybridizations using serial dilutions of the amplified/labeled nucleic acid.

The desired collection predetermined nucleic acid sequences, each of which characterizes a different biological entity or a variant of a biological entity, are selected from various sequence databases or printed publications. Such predetermined nucleic acid sequences are then either synthesized based upon the published nucleic acid sequence or cloned from appropriate sources (such as from the biological entity containing such nucleic acid sequence or from a cDNA or genomic library containing such nucleic acid sequence). Each selected predetermined nucleic acid sequence is amplified (e.g., using PCR and a primer pair which is specific for such predetermined nucleic acid sequence) to generate a sufficient quantity of such sequence for deposit on a solid substrate (e.g. a chip) and then isolated according to any of the well known techniques for isolation of DNA so that each deposit on the solid surface is free of impurities which could lead to a false indication that such predetermined nucleic acid sequence is present in a sample which is being tested. If desired one or more predetermined nucleic acid sequences could be combined in a single deposit on the solid surface, for example it may be deemed desirable to combine one or more variants of particular biological entity.

Numerous methods for the amplification and purification of nucleic acids are publicly available. The following protocol is merely illustrative.

Materials and Equipment

PCR primers modified with a 5'-amino-modifier C6 (Glen Research #10-1906-90)

Taq DNA polymerase (Stratagene #600139)
PCR Purification Kit (TeleChem #PCR-100)
Flat-bottom 384-well plates (Nunc #242765)
Micro-Spotting Solution (TeleChem #MSS-1).
Method
1. Add 1.0 microliter of DNA (10 ng/microliter) of the desired biological species from which the predetermined nucleic acid sequence is to be prepared into a reaction container. The DNA for each desired biological species is to be amplified in a separate reaction using primers (~21 mers) which are specific for the predetermined nucleic acid to be amplified.
2. Add 99.0 microliter of PCR mix which contains 10 microliter of lOX PCR buffer (500 mM KC 1, 100 mM Tris-Cl pH 8.3, 15 mM Mg2+, 0.1% gelatin), 10 microliter of dNTP cocktail (2 mM each), 1.0 microliter primer 1 (100 pmole/microliter), 1.0 microliter primer 2 (100 pmole/microliter), 1.0 microliter biological sample, 76 microliter H20, and 1.0 microliter Taq Polymerase (5 units/microliter).
3. Amplify the DNA using 30 rounds of PCR (94° C., 30 sec; 55° C., 30 sec; 72° C., 60 sec).
4: Purify the PCR products using a PCR Purification Kit.
5. Elute products with 100 microliter of 0.01×TE (pH 8.0).
6. Dry products to completion in a speedvac.
7. Resuspend each PCR product in 7.5 microliter Micro-Spotting solution.
8. Transfer to a flat bottom 384-well plate (Nunc) for arraying.
   a. Amino-linked cDNAs are made during PCR using primers that contain a C6 amino modifier (Glen Research) on the 5' end of each primer.
   b. Plasmid DNA can be prepared by alkaline lysis and purified. The 96 well REAL prep (Qiagen #SQ811 and #19504) facilitates rapid preparation.

Each of the collection of predetermined nucleic acid sequences are then spotted or printed onto a silica-based substrate or opaque membrane (nylon or nitrocellulose) using an arraying machine to create an array of predetermined nucleic acid sequences in a regular grid of hundreds to thousands of spots. The DNA in the spots may need to be bonded to the substrate to keep them from washing off during hybridization.

Numerous methods for the spotting or printing of nucleic acid sequences on a surface are publicly available. The following protocol is merely illustrative.

Reagents and Equipment
Micro-spotting robot (many models are available)
Stealth Micro Spotting Device (TeleChem)
SuperAldehyde Substrates (TeleChem)
Method
1. Obtain silylated (active aldehyde) microscope slides (CEL Associates).
2. Print amino-linked cDNAs using a micro-spotting device according the to manufacturer's instructions.
3. Allow printed microarrays to dry overnight in a slide box.
4. Soak slides twice in 0.2% SDS for 2 min at room temperature with vigorous agitation.
5. Soak slides twice in ddH20 for 2 min at room temperature with vigorous agitation.
6. Transfer slides into ddH20 at 95–100° C. for 2 min to allow DNA denaturation.
7. Allow slides to dry thoroughly at room temperature (~5 min).
8. Transfer slides into a sodium borohydride solution for 5 min at room temperature to reduce free aldehydes.
9. Rinse slides three times in 0.2%o SDS for 1 min each at room temperature.
10. Rinse slides once in ddHz0 for 1 min at room temperature.
11. Submerge slides in ddH20 at 95–100° C. for 2 seconds.
12. Allow the slides to air dry and store in the dark at 25° C. (stable for >1 year).
    a. Drying increases crosslinking efficiency. Several days or more is acceptable.
    b. This step removes salt and unbound DNA.
    c. Prepare sodium borohydride solution JUST PRIOR to use as follows. Dissolve 1.0 g NaBH4 in 300 ml phosphate buffered saline (PBS). Add 100 ml 100% ethanol to reduce bubbling.
    d. Heating the slides greatly aids in the drying process.

EXAMPLE 2

Use of a Diagnostic Array

An array, such as one prepared according to Example 1, would be utilized by preparing labeled nucleic acid from the sample to be screened, and hybridizing such labeled nucleic acid with the array. In addition labeled nucleic acid of the designated control sequences would be prepared (or in the event that the array is sold as part of a kit, could be supplied to the user).

Radioactive, calorimetric, chemiluminescent or fluorescent tags can be used for labeling of nucleic acid sequences from the sample and for the control. Numerous techniques for scanning arrays, detecting fluorescent, chemiluminescent, or colorimetric output, and analyzing results are being developed and commercialized. For example, GSI Lumonics has developed low-cost, high-throughput 2-, 3-, and 4-color laser scanning systems (ScanArray Systems). Numerous protocols for the preparation of labeled nucleic acid sequences are publicly available. The following protocols are provided for illustrative purposes: (i) a method for hybridization of fluorescently labeled sample to an array and analysis of the biological entities, (ii) a method of preparing fluorescently labeled nucleic acid from a sample and (iii) preparation of fluorescently labeled control nucleic acids.

1. Hybridization of Labeled Sample Nucleic Acid to Arrays and Analysis of Biological Entities.
Reagents and Equipment
Hybridization cassettes (TeleChem)
Array wash station (TeleChem)
Fluorescent labeled DNA derived from sample to be tested
Fluorescent labeled control nucleic acid sequences
ScanArray 3000,4000 or 5000 (GSI Lumonics)
Method
1. Place the array in a hybridization cassette. The array used in this example is a microarray that is 22×22 mm in size.
2. Add 5.0 microliter of 5×SSC+0.2% SDS to the slot in the cassette for humidification.
3. Pipette 6.0 microliter of fluorescent labeled nucleic acids derived from the sample, including a sufficient concentration of fluorescent labeled control nucleic acid, along the edge of a 22×22 mm cover slip.

4. Place the cover slip onto the microarray using forceps such that the sample forms a thin monolayer between the cover slip and the microarray.
5. Seal the hybridization cassette containing the microarray.
6. Submerge the hybridization cassette in a water bath set at 62° C.
7. Hybridize for 6 his at 62° C.
8. Following hybridization, remove the microarray from the hybridization cassette and place it immediately into the wash station.
9. Wash the microarray for 5 min at room temperature in 1×SSC+0.1% SDS.
10. Transfer the wash station and microarray to a second beaker containing 400 ml 0.1×SSC and 0.1% SDS.
11. Wash the microarray for 5 min. at room temperature 0.1×SSC and 0.1% SDS.
12. Rinse the microarray briefly in a third beaker containing 0.1×SSC to remove the SDS.
13. Allow the microarrays to air dry.
14. Scan the microarray with the ScanArray 3000, 4000 or 5000 to collect fluorescent emission.
15. Quantitate the fluorescent emission at each position within the microarray.
16. Assign gene expression values of the detected biological entities by comparing the experimental data to the appropriate controls.

Notes:
a. Cover slips must be free of oils, dust and other contaminants. Lower the cover slip onto the microarray from left to right so that the sample pushes out air bubbles as it forms a monolayer against the microarray surface. Small air bubbles trapped under the cover slip exit after several minutes at 62° C.
b. A temperature of 62° C. works well for cDNA-cDNA hybridizations. Lower temperatures should be used for hybridization to oligonucleotides.
c. Wash station should be placed in a 600 ml beaker containing 400 ml 1×SSC +0.1% SDS. The microarray should be transferred quickly from the cassette to the wash station. Leaving the microarray at room temperature will lead to elevated background fluorescence.
d. The cover slip should slide off the microarray during the wash step. If the cover slip does not slide off within 30 sec, use forceps to gently remove it from the microarray surface. Failure to remove the cover slip will prevent efficient washing of the microarray.

2. Preparation of Labeled Nucleic Acid from a Sample.
1. Prepare total nucleic acids from sample to be tested.
2. Amplify the nucleic acids by PCR using short random primers.
3. To a microfuge tube, add 71 microliter $H_2O$, 10 microliter 10× PCR buffer (500 mM KCl, 100 mM Tris-Cl pH 8.3, 15 mM $MgCl2$, 0.1% gelatin), 10 microliter dNTPs (2 mM each), 5 microliter Cy5-dCTP (1 mM)a, 2.0 microliter short random oligonucleotide primers (100 pmole/microliter), 1 microliter total nucleic acids from sample (0.5 microgram/microliter). Mix by tapping the microfuge tube gently.
4. Add 1.0 microliter Taq DNA polymerase (5 units/microliter). Mix by tapping the microfuge tube gently.
5. Generate fluorescent, single-stranded cDNAs by linear amplification of the total nucleic acids according to the following regime: [denature at 95° C. for 2 min, amplify for 30 cycles of (94° C. 30 sec, 55° C. 30 sec, 72° C. 30 sec), extend at 72° C. 3 min, hold at 4° until ready to purify].
6. Purify the fluorescent linear amplification products on a QIAquick column.
7. Evaporate the purified products to dryness on a speedvac.
8. Resuspend the pellet in 50 microliter of 1× TE (10 mM Tris-Cl and 1 mM EDTA) pH 8.0.

3. Preparation of Labeled Control Nucleic Acids.
Equipment and Reagents
Perkin Elmer 9600 Thermal Cycler (or equivalent)
QIAquick PCR purification kit (Qiagen #28106)
Method
1. Obtain a heterologous cDNA cloned into a plasmid vector.
2. Amplify the cDNA insert by PCR using cDNA-specific primers.
3. Purify the amplified cDNA insert using a QIAquick column.
4. Evaporate the sample to dryness in a speedvac.
5. Resuspend the purified cDNA insert in 10 microliter 1× TE (10 mM Tris-Cl and 1 mM EDTA) pH 8.0.
6. To a microfuge tube, add 71 microliter Hz0, 10 microliter 10× PCR buffer (500 mM KCl, 100 mM Tris-Cl pH 8.3, 15 mM $MgCl2$, 0.1% gelatin), 10 microliter dNTPs (2 mM each), 5 microliter Cy5-dCTP (1 mM)a, 2.0 microliter 20-mer oligonucleotide (100 pmole/microliter), 1 microliter cDNA PCR product (0.5 microgram/microliter). Mix by tapping the microfuge tube gently.
7. Add 1.0 microliter Taq DNA polymerase (5 units/microliter). Mix by tapping the microfuge tube gently.
8. Generate fluorescent, single-stranded cDNAs by linear amplification of the template according to the following regime: [denature at 95° C. for 2 min, amplify for 30 cycles of (94° C. 30 sec, 55° C. 30 sec, 72° C. 30 sec), extend at 72° C. 3 min, hold at 4° until ready to purify].
9. Purify the fluorescent linear amplification products on a QIAquick column.
10. Evaporate the purified products to dryness on a speedvac.
11. Resuspend the pellet in 50 microliter of 1× TE (10 mM Tris-Cl and 1 mM EDTA) pH 8.0. The concentration of the fluorescent, single-stranded cDNA should be ~40 ng/microliter.
12. Add 1.0 microliter of the 40 ng/microliter fluorescent control per 20 microliter hybridization buffer to provide a fluorescent, single-stranded cDNA control at ~2 ng/microliter.
a. Alternate fluors such as P12-dUTP, L5-dCTP and Cy5-dCTP can also be used.
b. Controls of this type provide a measure of hybridization and scanning, independent of an enzymatic labeling step such as reverse transcription. A 2 ng/microliter single-stranded product should produce an intense fluorescent signal equivalent to an abundant cellular transcript. Multiple fluorescent cDNAs can be used to generate a concentration series.

What is claimed is:
1. A method for detecting one or more biological entities in a sample, comprising:
(a) combining one or more nucleic acid sequences in a sample with multiple primers comprising randomized nucleotide sequences, said randomized sequences being sufficiently randomized such that substantially all of the nucleic acid sequences of a biological entity are represented among amplification products;

(b) randomly amplifying the sample nucleic acid sequences to produce nucleic acid amplification products;

(c) combining the amplification products with an array of predetermined nucleic acid sequences including redundancies which redundancies comprise multiple distinct nucleic acids from the same target entity and such that at least a portion of the amplification products hybridize to the array; and (d) detecting amplification products that hybridize to the array.

2. The method of claim 1, wherein a detectable nucleoside triphosphate is incorporated to produce detectable amplification products.

3. The method of claim 1, further comprising relating the detected amplification products to at least one biological entity in the sample.

4. The method of claim 1, wherein the primers are four to fifteen nucleotides in length.

5. The method of claim 1, wherein the array of predetermined nucleic acid sequences is immobilized on a surface.

6. The method of claim 2, wherein the detectable amplification products are enzymatically detected.

7. The method of claim 2, wherein the detectable nucleoside triphosphate is labeled with biotin.

8. The method of claim 2, wherein the detectable nucleoside triphosphate is fluorescently labeled.

9. The method of claim 2, wherein the detectable nucleoside triphosphate is labeled with digoxigenin.

10. The method of claim 1, wherein the detectable nucleoside triphosphate is labeled with radiolabel.

11. The method of claim 5, wherein the surface is an opaque membrane.

12. The method of claim 5, wherein the surface is silica-based.

13. The method of claim 1, wherein the predetermined nucleic acid sequences are at predetermined positions on the array and wherein the nucleic acid sequences at two or more predetermined positions characterize a different biological entity or variant of a biological entity.

14. The method of claim 1, further comprising relating the detected amplification products to the phylogeny of at least one biological entity.

15. The method of claim 1, wherein the biological entity comprises a pathogen.

16. The method of claim 1, wherein the predetermined nucleic acid sequences are more than 30 nucleotides in length.

17. A method for detecting one or more biological entities in a sample, comprising:

(a) combining one or more nucleic acid sequences in a sample with multiple primers comprising randomized nucleotide sequences, said randomized sequences being sufficiently randomized such that substantially all of the nucleic acid sequences of a biological entity are represented among amplification products;

(b) randomly amplifying the sample nucleic acid sequences to produce nucleic acid amplification products;

(c) combining the amplification products with an array of predetermined nucleic acid sequences including positive controls, negative controls and redundancies which redundancies comprises multiple distinct nucleic acids from the same target entity and such that at least a portion of the amplification products hybridize to the array; and (d) detecting amplification products that hybridize to the array.

18. The method of claim 17, wherein a detectable nucleoside triphosphate is incorporated to produce detectable amplification products.

19. The method of claim 17, further comprising relating the detected amplification products to at least one biological entity in the sample.

20. The method of claim 17, wherein the primers are four to fifteen nucleotides in length.

21. The method of claim 17, wherein the array of predetermined nucleic acid sequences is immobilized on a surface.

22. The method of claim 18, wherein the detectable amplification products are enzymatically detected.

23. The method of claim 18, wherein the detectable nucleoside triphosphate is labeled with biotin.

24. The method of claim 18, wherein the detectable nucleoside triphosphate is fluorescently labeled.

25. The method of claim 18, wherein the detectable nucleoside triphosphate is labeled with digoxigenin.

26. The method of claim 17, wherein the detectable nucleoside triphosphate is labeled with radiolabel.

27. The method of claim 21, wherein the surface is an opaque membrane.

28. The method of claim 21, wherein the surface is silica-based.

29. The method of claim 17, wherein the predetermined nucleic acid sequences are at predetermined positions on the array and wherein the nucleic acid sequences at two or more predetermined positions characterize a different biological entity or variant of a biological entity.

30. The method of claim 17, further comprising relating the detected amplification products to the phylogeny of at least one biological entity.

31. The method of claim 17, wherein the biological entity comprises a pathogen.

32. The method of claim 17, wherein the predetermined nucleic acid sequences are more than 30 nucleotides in length.

33. A method for detecting one or more biological entities in a sample, comprising:

(a) combining nucleic acid sequences in a sample with multiple primers comprising randomized nucleotide sequences, said randomized sequences being sufficiently randomized such that substantially all of the nucleic acid sequences of a biological entity are represented among amplification products;

(b) randomly amplifying the sample nucleic acid sequences to produce nucleic acid amplification products;

(c) combining the amplification products with an array of predetermined nucleic acid sequences having a know spatial arrangement or relationship to each other and further comprising redundancies which redundancies comprise multiple distinct nucleic acids from the same target entity and such that at least a portion of the amplification products hybridize to the array; and (d) detecting amplification products that hybridize to the array.

34. The method of claim 33 wherein a detectable nucleoside triphosphate is incorporated to produce detectable amplification products.

35. The method of claim 33, further comprising relating the detected amplification products to at least one biological entity in the sample.

36. The method of claim 33, wherein the primers are four to fifteen nucleotides in length.

37. The method of claim 33, wherein the array of predetermined nucleic acid sequences is immobilized on a surface.

38. The method of claim 34, wherein the detectable amplification products are enzymatically detected.

39. The method of claim 34, wherein the detectable nucleoside triphosphate is labeled with biotin.

40. The method of claim 34, wherein the detectable nucleoside triphosphate is fluorescently labeled.

41. The method of claim 34, wherein the detectable nucleoside triphosphate is labeled with digoxigenin.

42. The method of claim 34, wherein the detectable nucleoside triphosphate is labeled with radiolabel.

43. The method of claim 37, wherein the surface is an opaque membrane.

44. The method of claim 37, wherein the surface is silica-based.

45. The method of claim 33, wherein the predetermined nucleic acids are at predetermined positions on the array and wherein the nucleic acid sequences at two or more predetermined positions characterize a different biological entity or variant of a biological entity.

46. The method of claim 33, further comprising relating the detected amplification products to the phylogeny of at least one biological entity.

47. The method of claim 33, wherein the biological entity comprises a pathogen.

48. The method of claim 33, wherein the predetermined nucleic acid sequences are more than 30 nucleotides in length.

49. A method for detecting one or more biological entities in a sample, comprising:
(a) combining nucleic acid sequences in a sample with multiple primers comprising randomized nucleotide sequences, said randomized sequences being sufficiently randomized such that substantially all of the nucleic acid sequences of a biological entity are represented among amplification products;
(b) randomly amplifying the sample nucleic acid sequences at each cycle of the polymerase chain reaction, to produce nucleic acid amplification products;
(c) combining the amplification products with an array of predetermined nucleic acid sequences including redundancies which redundancies comprise multiple distinct nucleic acids from the same target entity and such that at least a portion of the amplification products hybridize to the array and wherein the redundancies on the array further comprise more than one copy of the same nucleic acid sequences; and
(d) detecting amplification products that hybridize to the array.

50. The method of claim 49 wherein a detectable nucleoside triphosphate is incorporated.

51. The method of claim 50, further comprising relating the detected amplification products to at least one biological entity in the sample.

52. The method of claim 49, wherein the primers are four to fifteen nucleotides in length.

53. The method of claim 49, wherein the array of predetermined nucleic acid sequences is immobilized on a surface.

54. The method of claim 50, wherein the detectable amplification products are enzymatically detected.

55. The method of claim 50, wherein the detectable nucleoside triphosphate is labeled with biotin.

56. The method of claim 50, wherein the detectable nucleoside triphosphate is fluorescently labeled.

57. The method of claim 50, wherein the detectable nucleoside triphosphate is labeled with digoxigenin.

58. The method of claim 49, wherein the detectable nucleoside triphosphate is labeled with radiolabel.

59. The method of claim 53, wherein the surface is an opaque membrane.

60. The method of claim 53, wherein the surface is silica-based.

61. The method of claim 49, wherein the predetermined nucleic acids are at predetermined positions on the array and wherein the nucleic acid sequences at two or more predetermined positions characterize a different biological entity or variant of a biological entity.

62. The method of claim 49, further comprising relating the detected amplification products to the phylogeny of at least one biological entity.

63. The method of claim 49, wherein the biological entity comprises a pathogen.

64. The method of claim 49, wherein the predetermined nucleic acid sequences are more than 30 nucleotides in length.

65. A method for detecting one or more biological entities of a plurality of preselected biological entities potentially present in a sample, comprising:
(a) combining nucleic acid sequences in a sample with multiple primers comprising randomized nucleotide sequences, said randomized sequences being sufficiently randomized such that substantially all of the nucleic acid sequences of a biological entity are represented among amplification products;
(b) randomly amplifying the sample nucleic acid sequences to produce nucleic acid amplification products;
(c) hybridizing the amplification products to an array of predetermined positions on the array in a predetermined pattern, wherein the nucleic acid sequences at the predetermined positions characterize at least one of the plurality of preselected biological entities and wherein the array comprises redundancies which redundancies comprise multiple distinct nucleic acids from the same target entity and
(d) detecting amplification products that hybridize to the array.

66. The method of claim 65, wherein a detectable nucleoside triphosphate is incorporated to produce detectable multiple amplification products.

67. The method of claim 65, wherein the method simultaneously detects two or more biological entities.

68. The method of claim 65, wherein the plurality of preselected biological entities is greater than twenty-five.

69. The method of claim 65, wherein the plurality of preselected biological entities is greater than fifty.

70. The method of claim 65, wherein the plurality of preselected biological entities is greater than one hundred.

71. The method of claim 65, wherein the plurality of preselected biological entities is greater than one thousand.

72. The method of claim 65, wherein the nucleic acid sequences at the predetermined positions comprise a continuum of highly conserved to highly specific nucleic acids.

73. The method of claim 65, wherein the method provides information about the biological entity.

74. The method of claim 65, wherein the method provides information on the biological entity including one or more of the following: the kingdom, phylum, class, order, family, genus and species of the biological entity.

75. The method of claim 65, wherein the method provides the ability to extract information resident in a genome of the biological entity.

76. The method of claim 65, wherein the method provides the ability to extract information about drug resistance of the biological entity.

77. The method of claim 65, wherein the method provides the ability to extract information about the identity of a pathogen present in of the biological entity.

78. The method of claim 65, wherein the method provides the ability to extract information about a pathogen comprising a communicable disease.

79. The method of claim 65, wherein the method provides the ability to extract information about treatment modalities for the biological entity.

80. The method of claim 65, wherein the method detects a genetic alteration in the biological entity.

81. The method of claim 65, wherein the method detects an induced genetic alteration in the biological entity.

82. The method of claim 65, wherein one or more of the predetermined nucleic acid sequences are redundant on the array.

83. The method of claim 65, wherein two or more of the predetermined nucleic acid sequences are overlapping sequences.

84. The method of claim 65, wherein two or more of the predetermined nucleic acid sequences are overlapping sequences of a single biological entity.

85. The method of claim 65, wherein two or more of the predetermined nucleic acid sequences are sub-sequences of each other.

86. The method of claim 65, wherein two or more of the predetermined nucleic acid sequences are nested subset sequences of each other.

87. The method of claim 65, wherein the detectable amplification products are hybridized to the array under high stringency conditions.

88. The method of claim 65, wherein the detectable amplification products are hybridized to the array under low stringency conditions.

89. The method of claim 65, wherein the detectable amplification products are hybridized to the array under hybridization conditions between about 50 and 65 degrees Celsius.

90. The method of claim 65, wherein the primers are four to fifteen nucleotides in length.

91. The method of claim 65, wherein the primers are four to nine nucleotides in length.

92. The method of claim 65, wherein the primers are four to six nucleotides in length.

93. The method of claim 65, wherein the primers are greater than six nucleotides in length.

94. The method of claim 2, wherein the detectable nucleoside triphosphate is incorporated during amplification.

95. The method of claim 18, wherein the detectable nucleoside triphosphate is incorporated during amplification.

96. The method of claim 34, wherein the detectable nucleoside triphosphate is incorporated during amplification.

97. The method of claim 50, wherein the detectable nucleoside triphosphate is incorporated during amplification.

98. The method of claim 66, wherein the detectable nucleoside triphosphate is incorporated during amplification.

99. A method for detecting one or more pathogens in a sample, wherein the pathogens are used for the production of biological weapons for terrorism or battlefield use, comprising:
  (a) combining one or more nucleic acid sequences in a sample with multiple primers comprising randomized nucleotide sequences, said randomized sequences being sufficiently randomized such that substantially all of the nucleic acid sequences of a biological entity are represented among amplification products;
  (b) randomly amplifying the sample nucleic acid sequences to produce nucleic acid amplification products;
  (c) combining the amplification products with an array of predetermined nucleic acid sequences including redundancies which redundancies comprise multiple distinct nucleic acids from the same target entity and such that at least a portion of the amplification products hybridize to the array; and
  (d) detecting amplification products that hybridize to the array.

100. The method of claim 99, wherein the biological pathogen comprises *Bacillus anthracis* or *Yersinia pestis*.

101. The method of claim 1 wherein the array provides broad identification, specific identification, or both broad and specific identification of the one or more biological entities detected.

102. The method of claim 1, wherein the primers are four to nine nucleotides in length.

103. The method of claim 1, wherein the primers are four to six nucleotides in length.

104. The method of claim 1, wherein the nucleic acid amplification products are produced by performing a plurality of cycles of a polymerase chain reaction to randomly amplify the sample nucleic acid sequences.

* * * * *

UNITED STATES PATENT AND TRADEMARK OFFICE
CERTIFICATE OF CORRECTION

PATENT NO. : 7,070,935 B2
APPLICATION NO. : 10/630384
DATED : July 4, 2006
INVENTOR(S) : Robert Paul Schaudies and Doreen Robinson It is certified that error appears in the above-identified patent and that said Letters Patent is hereby corrected as shown below:

On the Title Page
IN THE REFERENCES CITED (56) - OTHER PUBLICATIONS -

On Page 2, Column 1, Line 1 of the Ninteenth Reference, please change "Tetenius, et al., "Degenerate oligonucleotide primed PCR:" to -- Telenius, et al., "Degenerate oligonucleotide primed PCR: --

On Page 2, Column 2, Line 5 of the Third Reference, please change "Microbioloty, 32(3):596-602." to -- Microbiology, 32(3):596-602. --

IN THE CLAIMS:

In Column 12, Line 56 (Claim 33), please change "predetermined nucleic acid sequences having a know" to -- predetermined nucleic acid sequences having a known --

In Column 15, Line 13 (Claim 77), please change "pathogen present in of the biological entity." to -- pathogen present in the biological entity. --

Signed and Sealed this

Tenth Day of October, 2006

JON W. DUDAS
*Director of the United States Patent and Trademark Office*